US008048451B2

(12) United States Patent
Staniforth et al.

(10) Patent No.: US 8,048,451 B2
(45) Date of Patent: *Nov. 1, 2011

(54) PHARMACEUTICAL COMPOSITIONS FOR INHALATION (75) Inventors: John Nicholas Staniforth, Bath (GB); Haggis Harris, Bristol (GB); David Alexander Vodden Morton, Bath (GB); Robin Bannister, Essex (GB)

(73) Assignee: Vectura Limited, Wiltshire (GB)

( * ) Notice: Subject to any disclaimer, the term of this patent is extended or adjusted under 35 U.S.C. 154(b) by 151 days.

This patent is subject to a terminal disclaimer.

(21) Appl. No.: 10/433,185

(22) PCT Filed: Nov. 30, 2001

(86) PCT No.: PCT/GB01/05334
§ 371 (c)(1),
(2), (4) Date: Sep. 12, 2003

(87) PCT Pub. No.: WO02/43702
PCT Pub. Date: Jun. 6, 2002

(65) Prior Publication Data
US 2004/0047810 A1 Mar. 11, 2004

(30) Foreign Application Priority Data

| Nov. 30, 2000 | (GB) | ................................. 0029261.5 |
| Dec. 19, 2000 | (GB) | ................................. 0030946.8 |
| Apr. 9, 2001 | (WO) | ...................... PCT/GB01/01606 |
| Oct. 5, 2001 | (GB) | ................................. 0124010.0 |

(51) Int. Cl.
*A61K 9/14* (2006.01)
*A61K 9/16* (2006.01)
*A61K 9/00* (2006.01)

(52) U.S. Cl. ......................................... 424/489; 424/46
(58) Field of Classification Search .................... 424/46, 424/489
See application file for complete search history.

(56) References Cited

U.S. PATENT DOCUMENTS

| 4,906,476 | A | * | 3/1990 | Radhakrishnan | ............. 424/450 |
| 5,188,837 | A | * | 2/1993 | Domb | ............................ 424/450 |
| 5,192,528 | A | * | 3/1993 | Radhakrishnan et al. | ...... 424/45 |
| 5,320,906 | A | * | 6/1994 | Eley et al. | .................. 428/402.2 |
| 5,413,804 | A | | 5/1995 | Rhodes | ......................... 426/583 |
| 5,506,203 | A | | 4/1996 | Bäckström et al. | ............... 514/4 |
| 5,612,053 | A | | 3/1997 | Baichwal et al. | ............. 424/440 |
| 5,655,523 | A | | 8/1997 | Hodson et al. | ........... 128/203.15 |
| 5,663,198 | A | | 9/1997 | Reul et al. | ..................... 514/471 |
| 5,711,934 | A | * | 1/1998 | Adjei et al. | ..................... 424/45 |
| 5,738,865 | A | | 4/1998 | Baichwal et al. | ............. 424/440 |
| 5,931,809 | A | * | 8/1999 | Gruber et al. | .................. 604/512 |
| 5,935,555 | A | * | 8/1999 | Stutts et al. | ...................... 424/45 |
| 5,993,846 | A | | 11/1999 | Friedman et al. | ............. 424/434 |
| 5,997,848 | A | | 12/1999 | Patton et al. | ..................... 424/46 |
| 6,103,271 | A | * | 8/2000 | Morrison et al. | ............. 424/490 |
| 6,178,414 | B1 | | 1/2001 | Beckman et al. | ................. 707/3 |
| 6,197,369 | B1 | | 3/2001 | Watano et al. | ............... 427/213 |
| 6,404,772 | B1 | | 6/2002 | Beach et al. | ................... 370/338 |
| 6,475,523 | B1 | | 11/2002 | Staniforth et al. | ............ 424/70.1 |
| 6,477,670 | B1 | | 11/2002 | Ahmadvand | .................. 714/712 |
| 2003/0162835 | A1 | | 8/2003 | Staniforth et al. | ............. 424/46 |
| 2003/0165436 | A1 | | 9/2003 | Staniforth et al. | ............. 424/45 |
| 2003/0175214 | A1 | | 9/2003 | Staniforth et al. | ............. 424/45 |
| 2003/0185764 | A1 | | 10/2003 | Staniforth et al. | ............. 424/45 |
| 2004/0037785 | A1 | | 2/2004 | Staniforth et al. | ............. 424/46 |
| 2004/0071635 | A1 | | 4/2004 | Staniforth et al. | ............. 424/46 |
| 2004/0202616 | A1 | * | 10/2004 | Keller et al. | .................... 424/46 |
| 2005/0152849 | A1 | | 7/2005 | Staniforth | ..................... 424/489 |

FOREIGN PATENT DOCUMENTS

| EP | 025791581 | | 3/1993 |
| EP | 1430887 | | 6/2004 |
| WO | 9500127 | | 1/1995 |
| WO | 9619197 | | 6/1996 |
| WO | 9619198 | | 6/1996 |
| WO | 9623485 | | 8/1996 |
| WO | 9703649 | | 2/1997 |
| WO | 9938493 | | 8/1999 |
| WO | WO 00/27363 | * | 5/2000 |
| WO | WO 00/28969 | * | 5/2000 |
| WO | 0033811 | | 6/2000 |
| WO | WO 00061108 A1 | | 10/2000 |
| WO | 0230394 | | 4/2002 |

OTHER PUBLICATIONS

Merriam-Webster's Collegiate Dictionary, 10th ed., Merriam-Webster, Inc.: Springfield, Massachusetts, 1995, p. 739.*
Merriam-Webster Incorporated: Springfield, Massachusetts, 1993, pp. 311.*
International Search Report of International Application No. PCT/GB01/05305 (5 pages) (Jul. 18, 2002).
"Preparation for Inhalation: Aerodynamic Assessment of Fine Particles- Fine Particles Dose and Particle Size Distribution"; European Pharmacopeia (supplement 2000); Sec. 2.9.18.
William C. Hinds; "Aerosol Technology, Properties, Behavior and Measurement of Airborne Particles; Second edition"; John Wiley & Sons, Inc.(1999); pp. 51-52 and 402-408.

(Continued)

*Primary Examiner* — James H Alstrum Acevedo
(74) *Attorney, Agent, or Firm* — Davidson, Davidson & Kappel LLC (57) ABSTRACT

The invention provides microparticles for use in a pharmaceutical composition for pulmonary administration, each microparticle comprising a particle of an active substance having, on its surface, particles of a hydrophobic material suitable for delaying the dissolution of the active substance. The invention also provides a method for making the microparticles.

19 Claims, 6 Drawing Sheets

OTHER PUBLICATIONS

G. W. Hallworth et al, "The Twin Impinger: a Simple Device for Assessing the Delivery of Drugs from Metered Dose Pressurized Aerosol Inhalers"; J. Pharm. Pharmacol., vol. 39 (1987); pp. 988-972.

I. Colbeck; "Physical and Chemical Properties of Aerosols"; Blackie Academic & Professional; (Dec. 31. 1997) pp. 18-20.

Abstract of JP 05301810 Published Nov. 16, 1993.

Hamada, K. "The Surface Modification of Solid Particle by Adhesion of Liquid Using Hybridizer," Funtai Kagaku Kaishi, 1998, 35 (6), pp. 447-450 (English Abstract only).

Naito et al. The Iron Steel Institute of Japan International, 1993, 33(9), pp. 915-924.

\* cited by examiner

PHARMACEUTICAL COMPOSITIONS FOR INHALATION

The invention relates to pharmaceutical compositions for inhalation.

Pulmonary administration is known for the delivery of drugs for the treatment of respiratory conditions such as asthma and is receiving increasing attention as a route for the delivery of systemic drugs such as insulin. Known devices for the administration of drugs to the respiratory system include pressurised metered dose inhalers (pMDI's) and dry powder inhalers (DPI's).

In pulmonary administration, the size of the active particles is of great importance in determining the site of the absorption. In order that the particles be carried deep into the lungs, the particles must be very fine, for example having a mass median aerodynamic diameter of less than 10 μm. Particles having aerodynamic diameters greater than 10 μm are likely to impact the walls of the throat and generally do not reach the lung. Particles having aerodynamic diameters in the range of 5 μm to 0.5 μm will generally be deposited in the respiratory bronchioles whereas smaller particles having aerodynamic diameters in the range of 2 to 0.05 μm are likely to be deposited in the alveoli.

In an attempt to improve the flow of the powder, dry powders for use in dry powder inhalers often include particles of an excipient material mixed with the fine particles of active material. Such particles of excipient material may be coarse, for example having a mass median aerodynamic diameter greater than 90 μm, (such coarse particles are referred to as carrier particles) or they may be fine.

Propellant-based formulations for use with pressurised metered dose inhalers are also known and are widely used.

It has long been desired to develop pharmaceutical formulations in which the pharmaceutically active substance is released over a comparatively long period of time in order to maintain the concentration of the active substance in the blood at a desired level for a comparatively longer period of time. An associated benefit is an increase in patient compliance with the dosing regime brought about by reducing the number of, and/or the frequency of, the administrations necessary to maintain the concentration of the active substance in the blood at the desired level.

Delayed release compositions have been developed for delivery of drug to the gastrointestinal tract and some such compositions are commercially available. Systems for the controlled delivery of an active substance through the skin have also been developed.

Known techniques for preparing controlled release formulations can be categorised into one of two types. The first type involves the application of a barrier substance, in solution, to the active substance, for example, by spray drying or precipitation. The second type involves condensation of a barrier substance, from a vapour of the barrier substance, onto particles of active material.

However, there remains a need to develop a delayed release composition for pulmonary administration having satisfactory properties.

The present invention provides microparticles for use in a pharmaceutical composition for pulmonary administration, each microparticle comprising a particle of active substance having, on its surface, particles of a hydrophobic material suitable for delaying the dissolution of the active substance.

The term "microparticles" as used herein refers to particles of a size suitable for pulmonary administration or smaller, for example, having an MMAD of 10 μm or less.

The microparticles of the invention are able to release the active substance over a longer period than similarly-sized particles of the active substance alone and therefore a reduced frequency of administration, preferably only once a day or less, is possible. Furthermore, that delayed release of the active substance provides a lower initial peak of concentration of the active substance which may result in reduced side effects associated with the active substance.

The hydrophobic material will be suitable for delaying the dissolution of the active substance in an aqueous medium. A test method for determining whether a particular hydrophobic substance is suitable for delaying that dissolution is given below. The test may also be used for determining the extent of the reduction in the rate of dissolution and references herein to a reduction in that rate are to be understood as referring to the test given below. An alternative measure of hydrophobicity is the contact angle. The contact angle of a material is the angle between a liquid droplet and the surface of the material over which it spreads. The hydrophobic material preferably has a contact angle of more than 90°, more preferably more than 95° and most preferably more than 100°. The skilled person will be aware of suitable methods of measuring the contact angle for a particular substance.

The hydrophobic material will be pharmacologically acceptable for administration to the lungs in the amounts required according to the invention. Preferably, the hydrophobic material will not be sticky because sticky substances will tend to reduce dispersibility of the powder. Preferably, the hydrophobic material is a solid at room temperature.

Preferably, the hydrophobic material is one which is suitable for promoting the dispersal of the active particles on actuation of an inhaler.

The particles of hydrophobic material may include a combination of one or more substances. Preferably, all of those substances are hydrophobic materials but it is within the scope of the invention for the hydrophobic particles to include one or more substances which are not themselves hydrophobic, as long as the particles also contain materials which are hydrophobic in sufficient quantity that the mixture is hydrophobic as defined herein.

Preferably, the hydrophobic material is a naturally occurring animal or plant substance.

Advantageously, the hydrophobic material includes one or more compounds selected from hydrophobic amino acids and derivatives thereof, and hydrophobic peptides and polypeptides having a molecular weight from 0.25 to 1000 Kda, and derivatives thereof. Hydrophobic amino acids, peptides or polypeptides and derivatives of peptides or polypeptides are often physiologically acceptable.

It is advantageous for the hydrophobic material to comprise a hydrophobic amino acid. The additive material may comprise one or more of any of the following amino acids: tyrosine, tryptophan, glutamic acid, aspartic acid, leucine, isoleucine, lysine, valine, methionine, phenylalanine. The additive may be a salt or a derivative of an amino acid, for example, aspartame or acesulfame K. Preferred derivatives include salts, esters and amides. Preferably, the additive particles consist substantially of an amino acid, more preferably of leucine, advantageously L-leucine. The D- and DL-forms may also be used.

The hydrophobic material may have a limited degree of water solubility. This helps absorption of the hydrophobic substance by the body when the hydrophobic material reaches the lower lung. The hydrophobic material may, however, be insoluble in water, for example, the hydrophobic material may be magnesium stearate.

The hydrophobic material may comprise lecithin or a phospholipid or a derivative thereof such as an ester, amide or salt.

Preferably, the hydrophobic material comprises or consists of a $C_{10}$ to $C_{22}$ carboxylic acid which may be linear or branched, saturated or unsaturated or a derivative thereof such as an ester, amide or a salt.

Advantageously, the hydrophobic material comprises a metal stearate, or a derivative thereof, for example, sodium stearyl fumarate or sodium stearyl lactylate. Preferably, the hydrophobic material comprises a metal stearate. For example, magnesium stearate, calcium stearate, sodium stearate or lithium stearate. Preferably, the hydrophobic material comprises magnesium stearate.

The hydrophobic material may include or consist of one or more surface active materials, in particular materials that are surface active in the solid state, which may be water soluble to some degree, for example, lecithin, in particular soya lecithin, or substantially water insoluble, for example, solid state fatty acids such as oleic acid, behenic acid, or derivatives (such as esters and salts) thereof such as glyceryl behenate. Specific examples of such materials are: phosphatidylethanolamines, phosphatidylcholines, phosphatidylglycerols and other examples of natural synthetic lung surfactants; triglycerides such as DYNASAN® 118 and CUTINA® HR; and sugar esters in general, hydrogenated oils which are solid at room temperature, sorbitan esters which are solid at room temperature, cetyl stearyl alcohol and cetyl alcohol.

The hydrophobic material preferably comprises one or more materials selected from the group consisting of hydrophobic amino acids, lecithins, phospholipids, metal stearates (especially magnesium stearate), sodium stearyl fumarate, solid state fatty acids and glyceryl behenate.

The optimum amount of hydrophobic material will depend on, inter alia, the chemical composition and other properties of the hydrophobic material and upon the nature and particle size of the active material. In general, the amount of hydrophobic material in the composite particles will be not more than 90% by weight, based on the total weight of the microparticles.

Advantageously, the microparticles comprise not more than 80%, more preferably not more than 60%, more preferably not more than 40% by weight of the hydrophobic material, based on the total weight of the microparticles. The microparticles will usually comprise at least 0.01% by weight of the hydrophobic material and will preferably comprise at least 1%, more preferably at least 5% and optionally at least 15% by weight of the hydrophobic material, based on the total weight of the microparticles.

The microparticles advantageously comprise at least 0.1% by weight, preferably at least 1%, more preferably at least 10%, more advantageously at least 50% and especially advantageously at least 90% by weight of the active substance based on the total weight of the microparticles. The microparticles will, in general, not comprise more than 99.9% by weight of the active substance based on the total weight of the microparticles.

The mass median aerodynamic diameter of the microparticles is preferably not more than 10 μm, and advantageously not more than 5 μm, more preferably not more than 3 μm and may be less than 1 am. Accordingly, advantageously at least 90% by weight of the microparticles have a diameter of not more than 10 μm, advantageously not more than 5 μm, preferably not more than 3 μm and optionally not more than 1 μm. Advantageously, the microparticles will be the size of a suitable size for inhalation to the desired part of the lung, for example, having an MMAD in the range of 3 to 0.1 μm for absorption in the deep lung, 5 to 0.5 μm for absorption in the respiratory bronchioles, 10 to 2 μm for delivery to the higher respiratory system and 2 to 0.05 μm for delivery to the alveoli. Accordingly, advantageously at least 90% by weight of the microparticles have an aerodynamic diameter in the range of 3 to 0.1 μm, preferably 5 to 0.5 μm, advantageously 10 to 2 μm, and especially advantageously 2 to 0.05 μm. The MMAD of the microparticles will not normally be lower than 0.1 μm.

Alternatively, the microparticles may have diameters lower than the preferred range but may be present in the form of agglomerated microparticles, those agglomerated microparticles having mass median aerodynamic diameters in one of the ranges described above. The term "agglomerated microparticles" refers to particles which consist of more than one microparticle, those microparticles being adhered to each other. For example, an agglomerated microparticle of diameter 5 μm may consist of a large number of microparticles each having a diameter of 1 μm or less, adhered together. The agglomerated microparticles will normally be sufficiently stable that they do not break up during administration to the patient. The microparticles may also have on their surfaces a film forming material which may help to bind them together in an agglomerate.

Advantageously, the microparticles have at least a partial coating of a film-forming material which acts as a further barrier to the release of the active substance. The film-forming material will be pharmaceutically acceptable for administration to the lungs in amounts required in accordance with the invention. Suitable film forming materials are disclosed in U.S. Pat. No. 5,738,865 and U.S. Pat. No. 5,612,053 and include polysaccharides such as xanthan gum. Other preferred polysaccharides include derivatives of xanthan gum, such as deacylated xanthan gum, the carboxymethyl ether, the propylene glycol ester and the polyethylene glycol esters and galactomannan gums, which are polysaccharides composed solely of mannose and galactose. Locust bean gum, which has a higher ratio of mannose to the galactose, is especially preferred as compared to other galactomannans such as guar and hydroxypropyl guar.

Other naturally occurring polysaccharide gums known to those skilled in the food and pharmaceutical arts are also useful as the delayed release carrier of the invention. Such polysaccharides include alginic acid derivatives, carageenans, tragacanth, acacia, karaya, the polyethylene glycol esters of these gums, chitin, chitosan, mucopolysaccharides, konjac, starch, substituted starches, starch fragments, dextrins, British gums having a molecular weight of about 10,000 daltons, dextrans and the like. The starches can either be in native form i.e., ungelled starches such as potato, corn, rice, banana, etc., or gelled starches or semi-synthetic starches.

Starch and starch fragments are especially preferred polysaccharides and the combination of xanthan gum with locust bean gum is an especially preferred gum combination.

Other film-forming materials include pharmaceutically acceptable synthetic polymeric compounds such as polyvinylpyrrolidone (PVP) and protein materials such as albuimin and gelatin.

The film-forming material may be present in an amount of from 99% to about 10%, preferably from 50% to about 10%, by weight based on the total weight of the microparticles, that is, the total weight of the active substance and the hydrophobic material.

Preferably, the microparticles are such that, when inhaled, the active substance exerts its pharmacological effect over a period significantly greater (for example, greater by at least 20%, more preferably at least 50%) than the period over which the active substance exerts its pharmacological effect when inhaled alone (that is, when an equivalent quantity of the active substance is inhaled in the form of inhalable particles consisting of the active substance).

The invention will be of particular value where the active substance is one which exerts its pharmacological effect over a limited period and where, for therapeutic reasons, it is desired to extend that period. Preferably, the microparticles comprise an active substance that, when inhaled, exerts its pharmacological effect over a period of less than 12 hours, the microparticles being such that the active substance exerts its pharmacological effect over a period greater than 12 hours. The duration of the pharmacological effect for any particular active substance can be measured by methods known to the skilled person and will be based on the administration of the dose of that substance that is recognised as being optimal for that active substance in the circumstances. For example, where the active substance is salbutamol sulphate, the duration of the pharmacological effect will be measured by measuring the effect of administering a dose of the medically-recommended quantity of salbutamol upon the patients' respiratory volume. The means of measuring the duration of the period over which a particular active substance exerts its pharmacological effect will depend upon the nature of the active substance and may include, for example, the monitoring of variables relating to inhalation such as $FEV_1$ level where the active substance is one which exerts a pharmacological effect over the pulmonary system, for example, salbutamol. Further examples include the monitoring of blood sugar levels where the active substance is insulin or the subjective monitoring of pain relief by the patient where the active substance is an analgesic. Where it is not possible to unambiguously monitor the duration of the pharmacological effect of the active substance, for example, because that duration depends from instance to instance upon external factors beyond experimental control, the duration of the pharmacological effect may be assumed to be the same as the duration over which the active substance has the desired concentration in a relevant bodily fluid. Methods for measuring such concentrations are known to the skilled person. Advantageously, the microparticles are such that the active substance exerts its pharmacological effect over a period of at least 15 hours, preferably at least 24 hours.

Preferably, the microparticles are such that the rate of dissolution of the active substance (when tested according to the procedure given below) is no greater than 80%, more preferably no greater than 70%, advantageously no greater than 50% and most preferably no greater than 30%, of the rate of dissolution of particles of the active substance.

Optionally, the microparticles do not comprise an effective amount of an antimuscarinic substance. Optionally, the microparticles do not comprise an effective amount of glycopyrrolate. Optionally, the microparticles do not consist of a mixture of micronised glycopyrrolate and magnesium stearate in the ratio of 75:25 by mass. Suitable active substances include materials for therapeutic and/or prophylactic use. Active substances which may be included in the formulation include those products which are usually administered orally by inhalation for the treatment of disease such as respiratory disease, for example, β-agonists.

The active substance may be a $β_2$-agonist, for example, a compound selected from terbutaline, salbutamol, salmeterol and formeterol. If desired, the microparticles may comprise more than one of those active substances, provided they are compatible with one another under conditions of storage and use. Preferably, the active substance may be salbutamol sulphate. References herein to any active agent is to be understood to include any physiologically acceptable derivative. In the case of the $β_2$-agonists mentioned above, physiologically acceptable derivatives include especially salts, including sulphates.

The active substance may be a steroid, which may be beclomethasone dipropionate or may be fluticasone. The active substance may be a cromone which may be sodium cromoglycate or nedocromil. The active substance may be a leukotriene receptor antagonist.

The active substance may be a carbohydrate, for example heparin.

The active substance may advantageously comprise a pharmacologically active substance for systemic use and advantageously is capable of being absorbed into the circulatory system via the lungs. For example, the active substance may be a peptide or a polypeptide such as Dnase, leukotrienes or insulin. Preferably, the active substance is a biological macromolecule, for example, a polypeptide, a protein, or a DNA fragment. The active substance may be selected from the group consisting of insulin, human growth hormone, cytokines, cyclosporin, interferon, gonadotrophin agonists and antagonists, erythropoietin, leptin, antibodies, vaccines, antisense oligonucleotides, calcitonin, somotastatin, parathyroid hormone, alpha-1-antitrypsin, Factor 7, Factor 8, Factor 9, and estradiol. Advantageously the active substance is selected from the group consisting of insulin, human growth hormone, cytokines, cyclosporin, interferon, gonadotrophin agonists and antagonists, erythropoietin, leptin, antibodies, vaccines and antisense oligonucleotides. The microparticles of the invention may in particular have application in the administration of insulin to diabetic patients, preferably avoiding the normally invasive administration techniques used for that agent. The microparticles could also be used for pulmonary administration of other agents, for example, for pain relief (e.g. analgesics such as fentanyl or dihydroergotamine which is used for the treatment of migraine), anti-cancer activity, anti-virals, antibiotics or the local delivery of vaccines to the respiratory tract.

The active substance is present in the form of particles and at least some of the hydrophobic material is present on the surfaces of those particles of active substance. Such microparticles may be formed by dry mixing together particles of active substance and particles of hydrophobic substance or by combining particles of the hydrophobic substance with particles of active substance to form, in a liquid, a suspension, followed by the evaporation of the solvent to leave the particles of hydrophobic material on the surface of the particles of active substance.

The terms "active particles" and "particles of active substance" are used interchangeably herein. The active particles referred to throughout the specification will comprise one or more pharmacologically active substances. The active particles will advantageously consist essentially of one or more pharmacologically active substances.

The hydrophobic material may be in the form of a coating on the surfaces of the active particles. The coating may be a discontinuous coating. The hydrophobic material may be in the form of particles adhering to the surfaces of the particles of the active material. Furthermore, as explained above, at least some of the microparticles may be in the form of agglomerates.

The invention further provides a composition for inhalation comprising microparticles as described above. Preferably, the composition is a dry powder and is suitable for use in a dry powder inhaler. Such compositions may comprise essentially only the microparticles or they may comprise additional ingredients such as carrier particles and flavouring agents. Carrier particles may be of any acceptable excipient material or combination of materials. For example, the carrier particles may consist substantially of one or more materials selected from sugar alcohols, polyols and crystalline sugars. Other suitable carriers include inorganic salts such as sodium chloride and calcium carbonate, organic salts such as sodium lactate and other organic compounds such as polysaccharides and oligosaccharides. Advantageously, the carrier particles are of a polyol. In particular the carrier particles may consist substantially of a crystalline sugar, for example mannitol, dextrose or lactose. Preferably, the carrier particles are of lactose.

Advantageously, substantially all (by weight) of the carrier particles have a diameter which lies between 20 μm and 1000 μm, more preferably 50 μm and 1000 μm. Preferably, the diameter of substantially all (by weight) of the carrier particles is less than 355 μm and lies between 20 μm and 250 μm. Preferably at least 90% by weight of the carrier particles have a diameter between from 60 μm to 180 μm. The relatively large diameter of the carrier particles improves the opportunity for other, smaller particles to become attached to the surfaces of the carrier particles and to provide good flow and entrainment characteristics and improved release of the active particles in the airways to increase deposition of the active particles in the lower lung.

The ratio in which the carrier particles (if present) and microparticles are mixed will, of course, depend on the type of inhaler device used, the active substance used and the required dose. The carrier particles are preferably present in an amount of at least 50%, more preferably 70%, advantageously 90% and most preferably 95% based on the combined weight of the microparticles and the carrier particles.

Where carrier particles are included in the pharmaceutical composition, that composition preferably also includes small excipient particles having, for example, a particle size between 5 to 20 μm. Preferably the small excipient particles are present in an amount of from 1% to 40%, more preferably 5% to 20% based on the weight of the carrier particles.

The pharmaceutical composition may comprise a propellant and be suitable for use in a pressurised metered dose inhaler. The microparticles will be present as a suspension in the propellant and the composition may include one or more surfactants known in the art for stabilising such suspensions.

The invention further provides a method of preparing microparticles for use in a pharmaceutical composition for pulmonary administration, each microparticle comprising an active substance and a hydrophobic material suitable for delaying the dissolution of the active substance, the method comprising the step of combining the active substance with the hydrophobic material.

Preferably, as noted above, particles comprising the active substance are combined with particles of the hydrophobic material. Preferably, the active substance is milled in the presence of the hydrophobic material.

The word "milling" as used herein refers to any mechanical process which applies sufficient force to the particles of active material that it is capable of breaking coarse particles (for example, particles of mass medium aerodynamic diameter greater than 100 μm) down to fine particles of mass median aerodynamic diameter not more than 50 μm or which applies a relatively controlled compressive force as described below in relation to the MECHANO-FUSION™ and CYCLOMIX™ methods. It has been found that processes such as blending which do not apply a high degree of force are not effective in the method of the invention. It is believed that is because a high degree of force is required to separate the individual particles of active material and to break up tightly bound agglomerates of the active particles such that effective mixing and effective application of the hydrophobic material to the surfaces of those particles is achieved. It is believed that an especially desirable aspect of the milling process is that the hydrophobic material may become deformed in the milling and may be smeared over or fused to the surfaces of the active particles. It should be understood, however, that in the case where the particles of active material are already fine, for example, having a mass median aerodynamic diameter below 20 μm prior to the milling step, the size of those particles may not be significantly reduced. The important thing is that the milling process applies a sufficiently high degree of force or energy to the particles.

The method of the invention generally involves bringing the particles of hydrophobic material into close contact with the surfaces of the active particles. In order to achieve coated particles, a degree of intensive mixing is required to ensure a sufficient break-up of agglomerates of both constituents, dispersal and even distribution of additive over the host active particles.

Where the particles of hydrophobic material are very small (typically <1 micron), generally less work is required, firstly, as it is not required to break or deform but only to deagglomerate, distribute and embed the additive particles onto the active particle and, secondly, because of the naturally high surface energies of such small particles of hydrophobic material. It is known that where two powder components are mixed and the two components differ in size, there is a tendency for the small particles to adhere to the large particles (to form so called 'ordered mixes'). The short range Van der Waals interactions for such very fine components may be sufficient to ensure adhesion. However, where both the particles of hydrophobic material and active particles are very fine (for example less than 5 microns) a substantial degree of mixing will be required to ensure a sufficient break-up of agglomerates of both constituents, dispersal and even distribution of additive particles over the active particles as noted above. In some cases a simple contact adhesion may be insufficient and a stronger embedding or fusion of particles of hydrophobic material onto active particles is required to prevent segregation, or to enhance the structure and functionality of the coating.

Where the particles of hydrophobic material are not so small as to be sufficiently adhered by Van der Waals forces alone, or where there are advantages to distorting and/or embedding the particles of hydrophobic material substantially onto the host active particle, a greater degree of energy is required from the milling. In this case, the particles of hydrophobic material should experience sufficient force to soften and/or break, to distort and to flatten them. These processes are enhanced by the presence of the relatively harder active particles which act as a milling media as well as a de-agglomerating media for such processes. As a consequence of this process the particles of hydrophobic material may become wrapped around the core active particle to form a coating. These processes are also enhanced by the application of a compression force as mentioned above.

As a consequence of the milling step, complete or partial, continuous or discontinuous, porous or non-porous coatings may be formed. The coatings originate from a combination of active particles and particles of hydrophobic material. They are not coatings such as those formed by wet processes that require dissolution of one or both components. In general, such wet coating processes are likely to be more costly and more time consuming than the milling process and also suffer from the disadvantage that it is less easy to control the location and structure of the coating.

A wide range of milling devices and conditions are suitable for use in the method of the invention. The milling conditions, for example, intensity of milling and duration, should be selected to provide the required degree of force. Ball milling is a preferred method. Centrifugal and planetary ball milling are especially preferred methods. Alternatively, a high pressure homogeniser may be used in which a fluid containing the particles is forced through a constriction, such as, a valve at high pressure producing conditions of high shear and turbulence. Shear forces on the particles, impacts between the particles and machine surfaces or other particles and cavitation due to acceleration of the fluid may all contribute to the fracture of the particles and may also provide a compressive force. Such homogenisers may be more suitable than ball mills for use in large scale preparations of the composite active particles. Suitable homogenisers include EmulsiFlex® high pressure homogenisers which are capable of pressure up to 4000 Bar, Niro Soavi high pressure homogenisers (capable of pressures up to 2000 Bar), and Microfluidics Microfluidisers (maximum pressure 2750 Bar). The milling step may, alternatively, involve a high energy media mill or an agitator bead mill, for example, the Netzch high energy media mill, or the DYNO-mill (Willy A. Bachofen A G, Switzerland). Alternatively the milling may be a dry coating high energy process such as a MECHANO-FUSION™ system (Hosokawa Micron Ltd) or a Hybridizer (Nara). Other possible milling devices include air jet mills, pin mills, hammer mills, knife mills, ultracentrifugal mills and pestle and mortar mills.

Especially preferred methods are those involving the MECHANO-FUSION™, Hybridiser and CYCLOMIX™ instruments.

Preferably, the milling step involves the compression of the mixture of active particles and particles of hydrophobic material in a gap (or nip) of fixed, predetermined width (for example, as in the MECHANO-FUSION™ and CYCLOMIX™ methods described below).

Some preferred milling methods will now be described in greater detail.

MECHANO-FUSION™:

As the name suggests, this dry coating process is designed to mechanically fuse a first material onto a second. The first material is generally smaller and/or softer than the second. The MECHANO-FUSION™ and CYCLOMIX™ working principles are distinct from alternative milling techniques in having a particular interaction between inner element and vessel wall, and are based on providing energy by a controlled and substantial compressive force.

The fine active particles and the particles of hydrophobic particles are fed into the Fusion MECHANO-FUSION™ driven vessel, where they are subject to a centrifugal force and are pressed against the vessel inner wall. The powder is compressed between the fixed clearance of the drum wall and a curved inner element with high relative speed between drum and element. The inner wall and the curved element together form a gap or nip in which the particles are pressed together. As a result the particles experience very high shear forces and very strong compressive stresses as they are trapped between the inner drum wall and the inner element (which has a greater curvature than the inner drum wall). The particles violently collide against each other with enough energy to locally heat and soften, break, distort, flatten and wrap the particles of hydrophobic material around the core particle to form a coating. The energy is generally sufficient to break up agglomerates and some degree of size reduction of both components may occur. Embedding and fusion of particles of hydrophobic material onto the active particles may occur, facilitated by the relative differences in hardness (and optionally size) of the two components. Either the outer vessel or the inner element may rotate to provide the relative movement. The gap between these surfaces is relatively small, and is typically less than 10 mm and is preferably less than 5 mm, more preferably less than 3 mm. This gap is fixed, and consequently leads to a better control of the compressive energy than is provided in some other forms of mill such as ball and media mills. Also, preferably, no impaction of milling media surfaces is present so that wear and consequently contamination are minimised. The speed of rotation may be in the range of 200 to 10,000 rpm. A scraper may also be present to break up any caked material building up on the vessel surface. This is particularly advantageous when using fine cohesive starting materials. The local temperature may be controlled by use of a heating/cooling jacked built into the drum vessel walls. The powder may be re-circulated through the vessel.

CYCLOMIX™ Method (Hosokawa Micron):

The CYCLOMIX™ comprises a stationary conical vessel with a fast rotating shaft with paddles which move close to the wall. Due to the high rotational speed of the paddles, the powder is propelled towards the wall, and as a result the mixture experiences very high shear forces and compressive stresses between wall and paddle. Such effects are similar to the MECHANO-FUSION™ as described above and may be sufficient to locally heat and soften, to break, distort, flatten and wrap the particles of hydrophobic material around the active particles to form a coating. The energy is sufficient to break up agglomerates and some degree of size reduction of both components may also occur depending on the conditions and upon the size and nature of the particles.

Hybridiser Method:

This is a dry process which can be described as a product embedding or filming of one powder onto another. The fine active particles and fine or ultra fine particles of hydrophobic material are fed into a conventional high shear mixer pre-mix system to form an ordered mixture. This powder is then fed into the Hybridiser. The powder is subjected to ultra-high speed impact, compression and shear as it is impacted by blades on a high speed rotor inside a stator vessel, and is re-circulated within the vessel. The active particles and particles of hydrophobic material collide with each other. Typical speeds of rotation are in the range of 5,000 to 20,000 rpm. The relatively soft fine additive particles experience sufficient impact force to soften, break, distort, flatten and wrap around the active particle to form a coating. There may also be some degree of embedding into the surface of the active particles.

Other preferred methods include ball and high energy media mills which are also capable of providing the desired high shear force and compressive stresses between surfaces, although as the clearance gap is not controlled, the coating process may be less well controlled than for Mechano-Fusion milling and some problems such as a degree of undesired re-agglomeration may occur. These media mills may be rotational, vibrational, agitational, centrifugal or planetary in nature.

It has been observed in some cases that when ball milling active particles with hydrophobic material, a fine powder is not produced. Instead the powder was compacted on the walls of the mill by the action of the mill. That has inhibited the milling action and prevented the preparation of the microparticles. That problem occurred particularly when certain hydrophobic materials were used, in cases where the hydrophobic material was present in small proportions (typically <2%), in cases where the milling balls were relatively small (typically <3 mm), in cases where the milling speed was too slow and where the starting particles were too fine. To prevent this occurring it is advantageous to ball mill in a liquid medium. The liquid medium reduces the tendency to compaction, assists the dispersal of hydrophobic material and improves any milling action.

It has been found to be preferable to use a large number of fine milling balls, rather than fewer heavy balls. The finer balls perform a more efficient co-milling action. Preferably the balls have a diameter of less than 5 mm, advantageously less than 2 mm. Liquid media are preferred which do not dissolve the active material and which evaporate rapidly and fully, for example non-aqueous liquids such as diethylether, acetone, cyclohexane, ethanol, isopropanol or dichloromethane. Liquid media are preferred which are non flammable, for example dichloromethane and fluorinated hydrocarbons, especially fluorinated hydrocarbons which are suitable for use as propellants in inhalers.

Pestle and mortar mills are other mills which also provide a very high shear force and compressive stresses between surfaces.

Mechano-Micros and Micros mills made by Nara (where particles are compressed by rotating grinding rings) may also be used. Mills referred to as impact mixers, attrition mills, pin mills and disc mills may also be used.

The mass median aerodynamic diameter of the particles of active material may be substantially reduced during the milling step especially when the active material is in the form of coarse particles prior to the milling step. The mass median aerodynamic diameter (MMAD) of the particles of active material may be reduced by at least 10%, by at least 50%, or by at least 70% during the milling step depending on the milling conditions and the MMAD of the active particles prior to the milling step.

Advantageously, after the milling step, the MMAD of the active particles is less than 9 µm, preferably less than 4 µm and more preferably less then than 2 µm.

In a similar way, where the hydrophobic material is in the form of coarse particles prior to the milling step, their MMAD will be substantially reduced during the milling step. The MMAD of the particles of hydrophobic material may be reduced by at least 10%, at least 50% or at least 70% during the milling step, depending on the milling conditions and on the MMAD of the particles of hydrophobic material before the milling step.

The size of the particles of hydrophobic material after the milling step is preferably significantly less than the size of the active particles, to enable the hydrophobic materials to more effectively coat the surfaces of the active particles. In practice, that difference in size between the active particles and particles of hydrophobic material will be achieved as a consequence of the milling because the hydrophobic material will usually be more easily fractured or deformed than the active material and so will be broken into smaller particles than the active material. As noted above, the particles of hydrophobic material preferably become smeared over or fused to the surfaces of the particles of active material, thereby forming a coating which may be substantially continuous or discontinuous. Where the coating is discontinuous, it preferably covers on average of at least 50% (that is, at least 50% of the total surface area of the active particles will be covered by additive material), more advantageously at least 70% and most preferably at least 90% of the surfaces of the active particles. The coating is preferably on average less than 1 µm, more preferably less than 0.5 µm and most preferably less than 200 nm thick.

The milling step may be carried out in a closed vessel, for example in a ball mill or a MECHANO-FUSION™ device. The use of a closed vessel prevents loss of ultrafine particles or vapour of the hydrophobic material which has been found to occur in jet milling or other open processes. Preferably, the milling is not jet milling (micronisation).

The milling may be wet milling, that is, the milling step may be carried out in the presence of a liquid. That liquid medium may be high or low volatility and of any solid content as long as it does not dissolve the active particles to any significant degree and its viscosity is not so high that it prevents effective milling. The liquid medium preferably is not aqueous. The liquid is preferably one in which the hydrophobic material is substantially insoluble but some degree of solubility may be acceptable as long as there is sufficient hydrophobic material present that undissolved particles of hydrophobic material remain. The presence of a liquid medium helps to prevent compacting of the particles of active material on the walls of the vessel and may also allow the more even spreading of the hydrophobic material on the surface of the particles of active material as compared to dry milling.

It has been found that the MECHANO-FUSION™ and CYCLOMIX™ techniques referred to above often provide the microparticles as individual, that is, unagglomerated microparticles. That is in contrast to less controlled methods such as ball milling, which have been found to often produce the microparticles in the form of agglomerated microparticles.

Alternatively, particles comprising the active substance are combined with the particles of hydrophobic material in a spray drying step, that is, by spray drying a suspension comprising the particles of active substance and particles of hydrophobic substances. The film forming material, if present, will be dissolved in the suspension. The skilled person will be able to select appropriate spray drying conditions. A number of commercially available spray drying machines can be used to prepare the microparticles of the invention, for example, suitable machines are manufactured by Buchi and Niro. In a typical spray drying machine the suspension to be dried is pumped from a stirred reservoir to an atomisation chamber where it is sprayed from a nozzle as fine droplets (preferably the droplets are in the range of 1 to 20 µm in diameter) into a stream of heated air, for example, inlet temperatures in the range of 50 to 150° C. (nitrogen can be used in place of air if there is a risk of undesirable oxidation of the active substance). The temperature of the heated air must be sufficient to evaporate the liquid and dry the microparticles to a free flowing powder but should not be so high as to degrade the active substance. The microparticles may be collected in a cyclone or a filter or a combination of cyclones and filters.

The invention also provides a method of pulmonary administration of an active substance comprising the step of administering microparticles as described above to a person in need thereof.

The invention also provides the use of a hydrophobic material in a pharmaceutical composition comprising an active substance for pulmonary administration, to delay the dissolution of the active substance in the lung. Preferably, the use of the hydrophobic substance reduces the rate of dissolution of the active substance by at least 20%, preferably at least 30% and more preferably by at least 50%.

According to a further aspect of the invention, a pharmaceutical composition for pulmonary delivery comprises an active substance that exerts a pharmacological effect over a period less than 12 hours, in a delayed release formulation, wherein, on administration, the formulation permits the active substance to exert its pharmacological effect over a period greater than 12 hours.

The delayed release formulation will preferably comprise or consist of microparticles as described above.

Embodiments of the invention will now be described for the purposes of illustration only with reference to the Figures in which.

EXAMPLE 1a 5 g of micronised salbutamol sulphate (particle size distribution: 1 to 5 μm) and 0.5 g of magnesium stearate were added to a 50 cm$^3$ stainless steel milling vessel together with 20 cm$^3$ dichloromethane and 124 g of 3 mm stainless steel balls. The mixture was milled at 550 rpm in a Retsch S100 Centrifugal Mill for 5 hours. The powder was recovered by drying and sieving to remove the mill balls. The powders were examined using a scanning electron microscope and were found to have particles in the size range 0.1 to 0.5 μm.

EXAMPLE 1b

Micronised salbutamol sulphate and magnesium stearate were combined as particles in a suspension in the ratio 10:1 in propanol. This suspension was processed in an EmulsiFlex® C50 high pressure homogeniser by 5 sequential passes through the system at 25,000 psi. This dry material was then recovered by evaporating the propanol.

EXAMPLE 1c

It was found that, on drying, the powder prepared in Example 1a including magnesium stearate as additive material formed assemblies of primary particles which were hard to deagglomerate. A sample of this powder was re-dispersed by ball milling for 90 minutes at 550 rpm in a mixture of ethanol, polyvinylpyrrolidone (PVPK30) and HFA227 liquid propellant to give the following composition:

| 0.6% | w/w | Salbutamol sulphate/magnesium stearate microparticles |
|---|---|---|
| 0.2% | w/w | PVPK30 |
| 5.0% | w/w | Ethanol |
| 94.2% | w/w | HFA 227 |

(The PVP was included to stabilise the suspension of the microparticles in the ethanol/HFA227).

The composition was sprayed from a pressurised can through an orifice ~0.4 mm in diameter to produce dried microparticles of salbutamol sulphate and magnesium stearate with PVP. Those particles were collected and examined and were found to be in the aerodynamic size range 0.1 to 4 μm.

EXAMPLE 2

The process of Example 1c was repeated except that the composition was as follows:

| | | |
|---|---|---|
| 3% | w/w | Salbutamol sulphate/magnesium stearate microparticles |
| 1% | w/w | PVPK30 |
| 3% | w/w | Ethanol |
| 93% | w/w | HFA 227 |

Similarly, a sample was redispersed in dichloromethane and spray dried.

EXAMPLE 3

A mixture of micronised glycopyrrolate and magnesium stearate in the ratio 75:25 by mass (total mass of approximately 1 g) was placed in a ball mill on top of 100 g of 2 mm stainless steel balls. The mill volume was approximately 58.8 $cm^3$. 5 $cm^3$ of cyclohexane was added to wet the mixture. The mill was sealed and secured in a Retsch S100 centrifuge. Centrifugation was then carried out at 500 rpm for 240 minutes in total. Small samples (approximately 5-10 mg) of wet powder were then removed from the mill every 60 minutes. The samples were dried in an oven at 37° C. under a vacuum, prior to using the samples in the dissolution test.

The samples were analysed in a Cecil Aquarius CE7200 ultraviolet spectrophotometer at a wavelength of 200 nm. The concentration of the samples was calculated with a previously prepared calibration graph and the concentration versus time was plotted. To establish the base line diffusion characteristics of the system, 1 $cm^3$ aqueous solution containing 1 mg of glycopyrrolate was added to the system and the samples taken as above. The results are shown in FIG. 2.

FIG. 2 shows that the sample containing only glycopyrrolate exhibited a quick release of the glycopyrrolate into the reservoir, with the first time point at 5 minutes showing a concentration of greater than 10 mg/l. In contrast, the glycopyrrolate/magnesium stearate composition showed the delayed release properties, with a concentration at 5 minutes of approximately 3.7 mg/l. The maximum concentration is achieved after 40 minutes in contrast to that of glycopyrrolate only, which achieves the maximum concentration at only 10 minutes.

EXAMPLE 4

Salbutamol Sulphate/Magnesium Stearate Blends a) Homogenised Magnesium Stearate 240 g magnesium stearate (Riedel de Haen, particle size by Malvern laser diffraction: $d_{50}$ 9.7 μm) was suspended in 2150 g dichloroethane. That suspension was then mixed for 5 minutes in a Silverson high shear mixer. The suspension was then processed in an EmulsiFlex® C50 high pressure homogeniser fitted with a heat exchanger at 10000 psi for 20 minutes in circulation mode (300 $cm^3$/min) for 20 minutes. The suspension was then circulated at atmospheric pressure for 20 minutes allow it to cool. The next day, the suspension was processed in circulation mode (260 $cm^3$/min) at 20000 psi for 30 minutes. The dichloroethane was removed by rotary evaporation followed by drying in a vacuum over at 37° C. overnight. The resulting cake of material was broken up by ball milling for 1 minute. The homogenised magnesium stearate had a particle size of less than 2 μm.

b) A 9:1 by weight blend of salbutamol sulphate and homogenised magnesium stearate having a particle size of less than 2 μm was prepared by blending the two materials with a spatula. An electron micrograph of the blended material showed that the blend was mostly in the form of agglomerated particles, the agglomerates having diameters of 50 μm and above. The blend was then processed in a MECHANO-FUSION™ mill (Hosokawa) as follows:

| Machine data: | Hosokawa Mechano-Fusion: | AMS-Mini |
|---|---|---|
| | Drive: | 2.2 kW |
| | Housing: | stainless steel |
| | Rotor: | stainless steel |
| | Scraper: | None |
| | Cooling: | Water |
| | Gas purge: | None |

Figure 5:
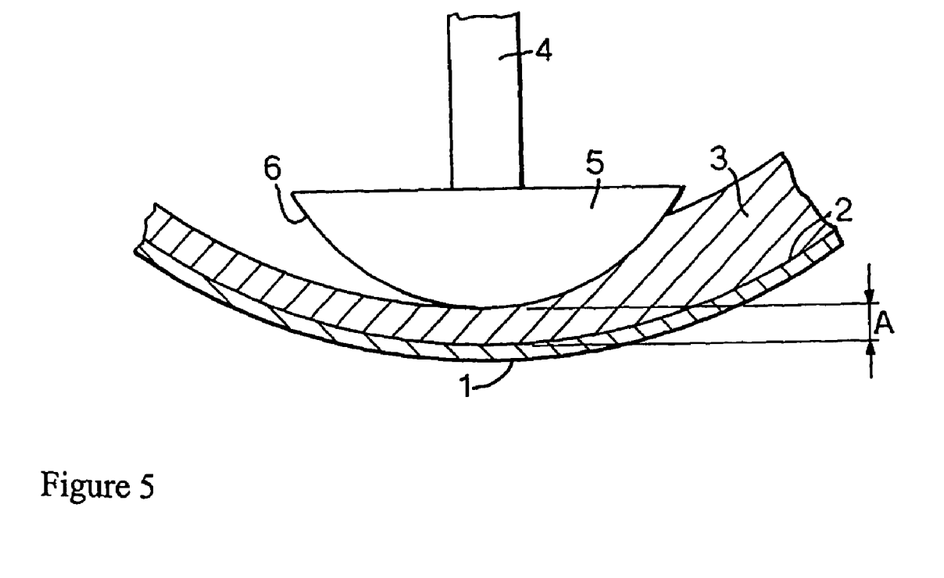
FIG. 5 is a schematic drawing of part of a Mechano-Fusion machine.

The MECHANO-FUSION™ device (see FIG. 5) comprises a cylindrical drum 1 having an inner wall 2. In use, the drum rotates at high speed. The powder 3 of the active and additive particles is thrown by centrifugal force against the inner wall 2 of the drum 1. A fixed arm 4 projects from the interior of the drum in a radial direction. At the end of the arm closest to the wall 2, the arm is provided with a member 5 which presents an arcuate surface 6, of radius of curvature less than that of inner wall 2, toward that inner wall. As the drum 1 rotates, it carries powder 3 into the gap between arcuate surface 6 and inner wall 2 thereby compressing the powder. The gap is of a fixed, predetermined width A. A scraper (not shown in FIG. 5) may be provided to scrape the compressed powder from the wall of the drum.

All samples were premixed for 5 minutes by running the machine at 1000 rpm. The machine speed was then increased to 5050 rpm for 30 minutes. The procedure was repeated for salbutamol sulphate/magnesium stearate in the following weight ratios: 19:1, 3:1, 1:1.

Figure 6:
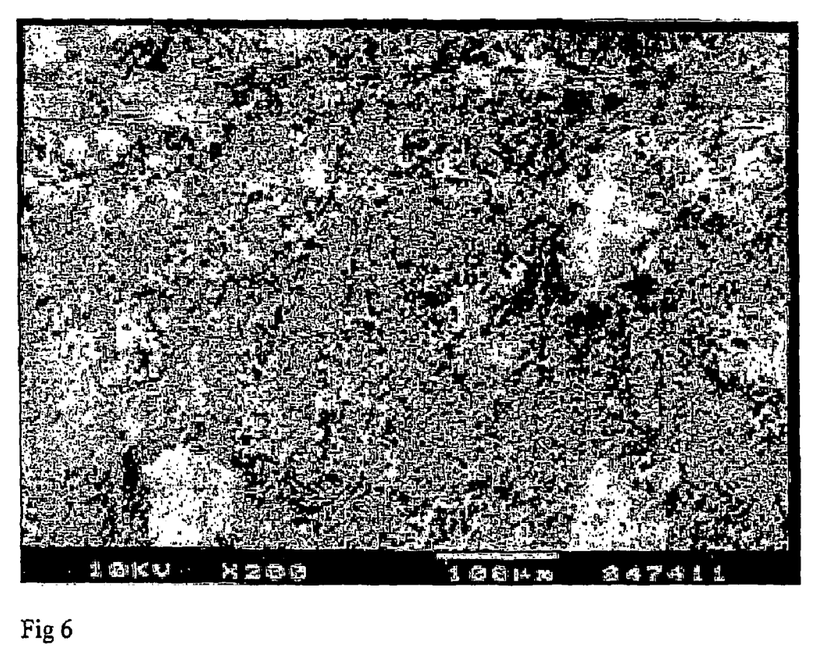
FIGS. 6 and 7 are electron micrographs of composite active particles according to the invention comprising salbutamol sulphate and magnesium stearate in a ratio of 19:1.
Figure 7:
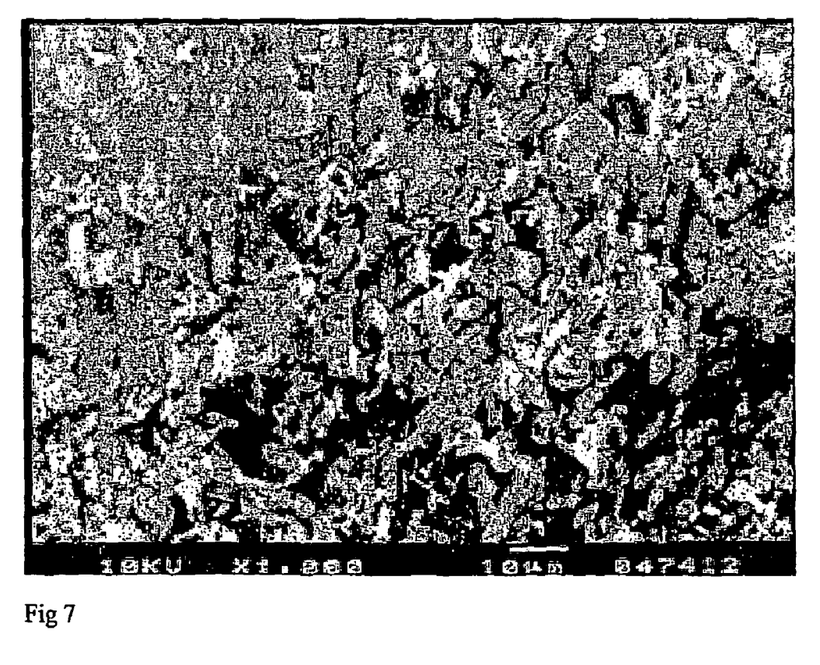

Electronmicrographs of the 19:1 processed material are shown in FIGS. 6 and 7 and indicate that the material was mostly in the form of simple small particles of diameter less than 5 μm or in very loose agglomerates of such particles with only one agglomerate of the original type being visible.

The 3:1 and the 19:1 blends were then each loaded into a 20 mg capsule and fired from a twin stage impinger. A sample of unprocessed salbutamol sulphate was also fired from the TSI to provide a comparison.

The fine particle fractions were then calculated and are given in table 1.

TABLE 1

Fine Particle Fraction results for salbutamol sulphate blends.

| Composition | Fine Particle Fraction % |
|---|---|
| salbutamol sulphate | 28 |
| salbutamol sulphate/magnesium stearate 19:1 | 66 |
| salbutamol sulphate/magnesium stearate 3:1 | 66 |

Figure 3:
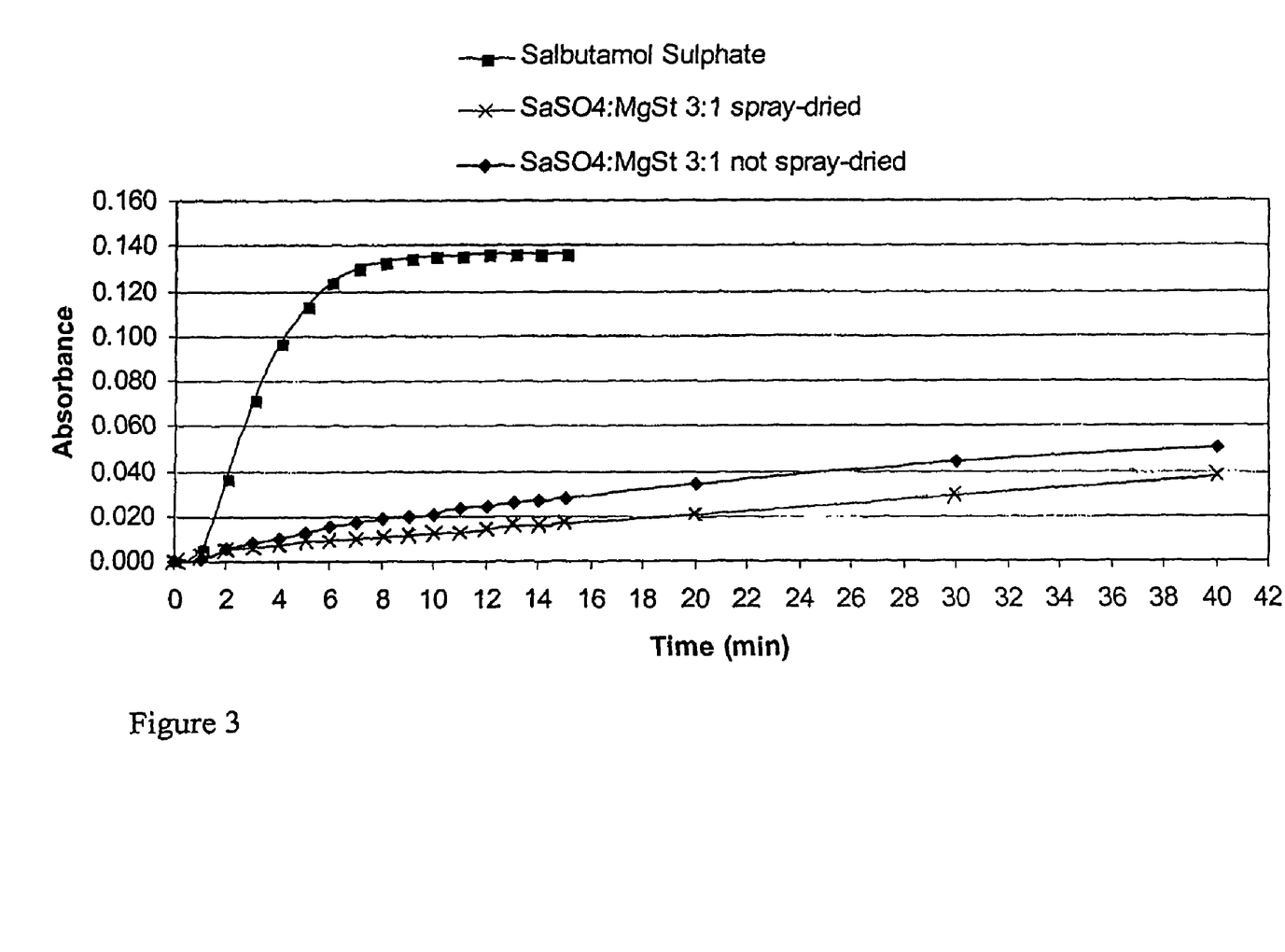
FIG. 3 shows dissolution curves for salbutamol sulphate and salbutamol sulphate/magnesium stearate blends.

A 1 g sample of the 3:1 blend was suspended by ball milling in 10 cm³ dichloromethane for 5 minutes. The suspension was then spray dried on a Buchi B191 spray dryer using the following conditions inlet T=50° C., aspirator 100%, liquid flow 10 cm³/min nozzle air flow 800 cm³/hr. The 3:1 blend, the spray dried 3:1 blend and a sample of salbutamol sulphate were then each tested for dissolution rate using the procedure outlined above. The results are shown in FIG. 3. It is clear from FIG. 3 that the 3:1 blend of salbutamol sulphate:magnesium stearate dissolves at a significantly slower rate than the salbutamol sulphate with no magnesium stearate. That delayed dissolution effect is shown by the spray dried sample of the 3:1 blend. That contrasts to the results of similar experiments carried out using blends of drug and magnesium stearate where the magnesium stearate has not been homogenised (and does not have a particle size below 2 μm) in which spray drying of the blend has produced a significant decrease in the extent of the delayed dissolution effect.

Figure 4:
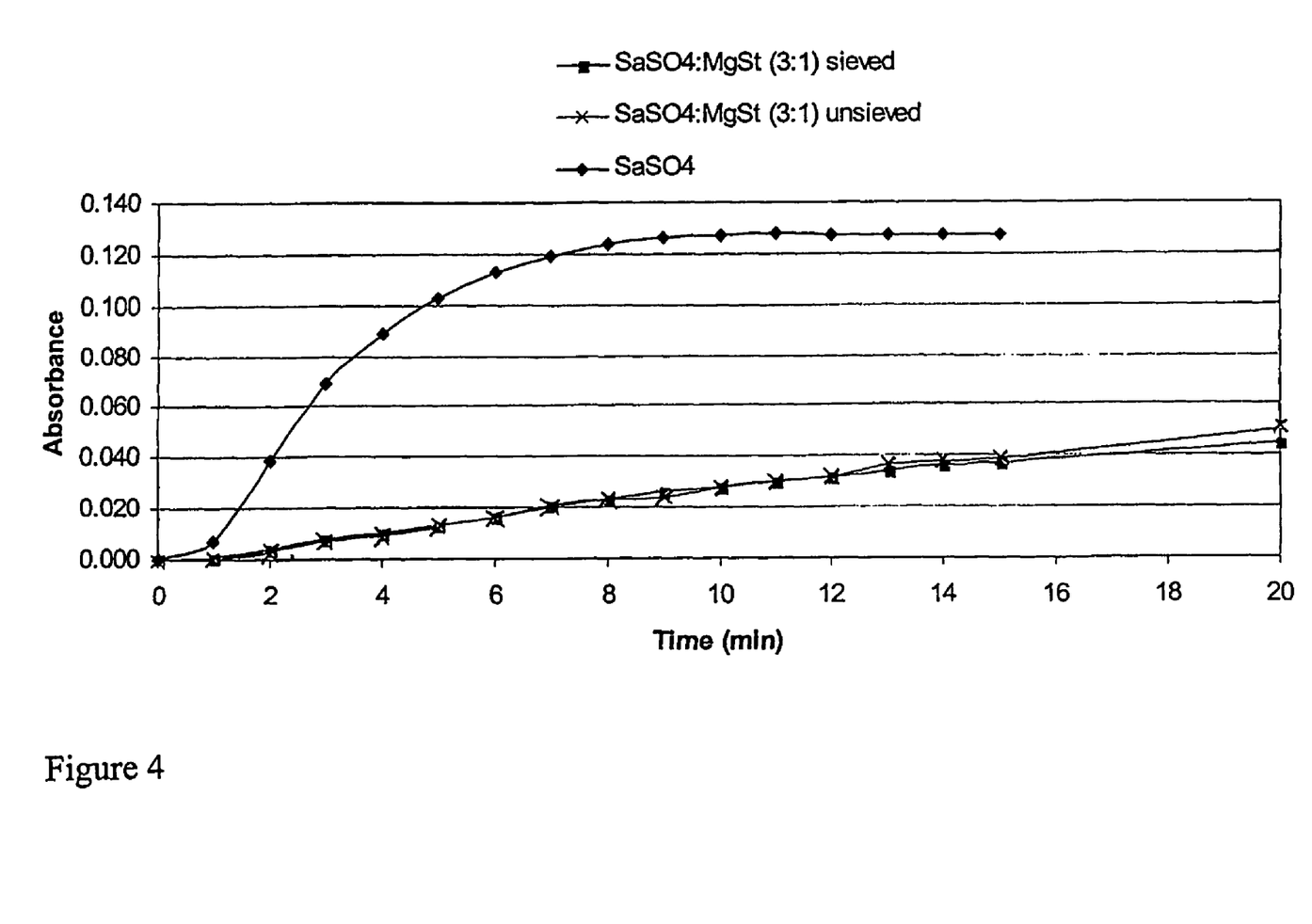
FIG. 4 shows dissolution curves for sieved and unsieved blends of salbutamol sulphate and magnesium stearate.

To test the effect of any agglomeration in the blend upon the dissolution rate of the salbutamol sulphate in the blends a sample of the 3:1 salbutamol sulphate:magnesium stearate blend was brushed through a 45 μm sieve. FIG. 4 shows the dissolution curves for the sieved and unsieved blends and for salbutamol sulphate. It can be seen that the sieved and unsieved 3:1 blends had the same dissolution rate.

1) Standard Dissolution Test

This test is used as a model test for the length of time taken for a particular formulation to dissolve on the lung membrane.

Figure 1:
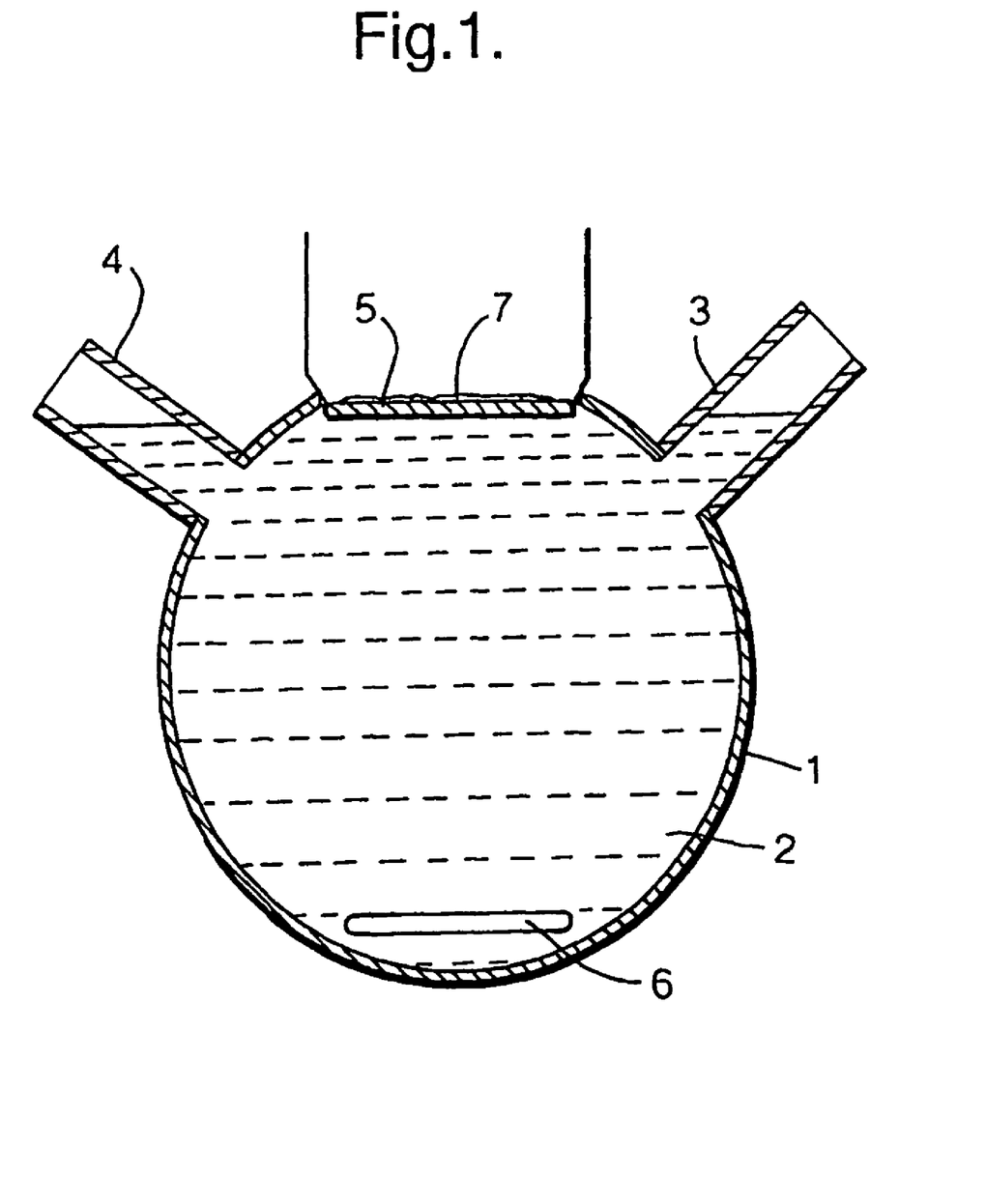
FIG. 1 shows an apparatus used in the dissolution test.
Figure 2:
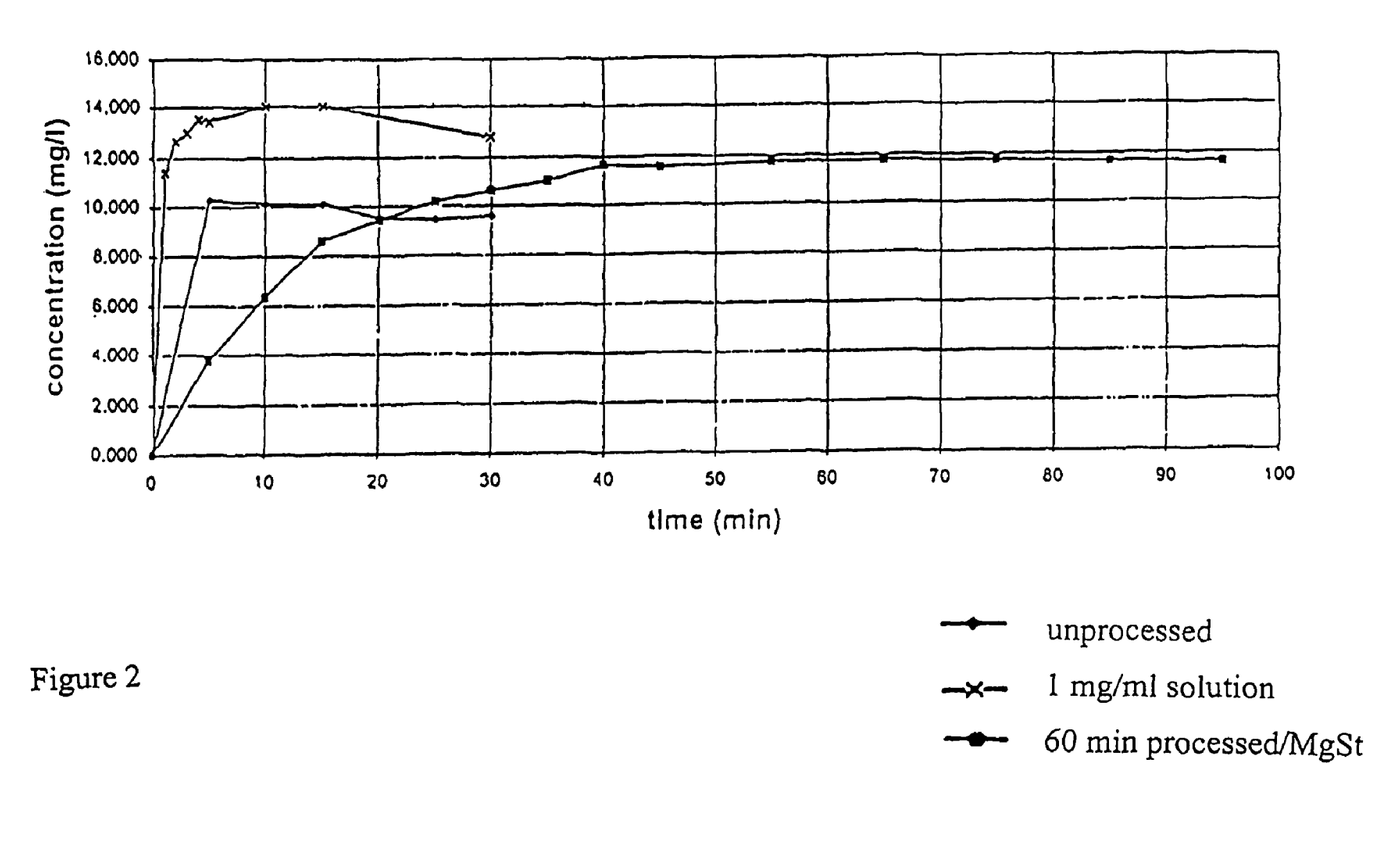
FIG. 2 shows the results of the dissolution test on the formulations of Example 3.

The apparatus used is shown in FIG. 1 and comprises a 195 cm³ reservoir (1) filled with deionised water (2) and having an inlet port (3) and an outlet port (4). A sintered glass disc (5) of approximately 50 mm diameter and 3 mm depth occupies an opening at the top of the reservoir (1) and sits horizontally in contact with the water (2). The water in the reservoir is stirred by a magnetic stirrer (6).

A known mass of approximately 1 mg of the formulation (7) to be tested is placed on the sinter and a timer is started. At various times, 1 cm³ samples of the water are removed from the reservoir and are immediately replaced with 1 cm³ deionised water to maintain the volume in the reservoir. The concentration of the active substance in the 1 cm³ samples is determined by a suitable method. The particular method will, of course, depend on the nature of the active substance but such methods will be known to the skilled person.

A graph of concentration of the active substance in the reservoir of water versus time is then plotted.

2) Standard Formulation Test

In order to determine whether or not a particular hydrophobic material is suitable for delaying the dissolution of the active substance, the following test is carried out.

A standard test formulation is prepared in the following manner:

A mixture of salbutamol sulphate and the material to be tested in the ratio of 75:25 by mass (total mass of approximately 1 g) is placed in a ball mill chamber on top of 100 g of 2 mm diameter stainless steel balls. The mill chamber volume is approximately 58.8 cm³. 5 cm³ of an inert non-solvent is added to wet the mixture; The mill is sealed and secured in a Retsch S100 centrifuge. Centrifugation is then carried out at 500 rpm for 240 minutes in total. A small sample (approximately 5-10 mg) of wet powder is removed from the mill after 60 minutes. The sample is then dried in an oven at 37° C. under vacuum for 2 hours or as long as necessary to remove the inert non-solvent.

Where the hydrophobic material is such that no suitable non-solvent can be found, the mixture of salbutamol sulphate and the hydrophobic material is combined in a Mechano-Fusion apparatus as described above in example 4b).

The dry powder is then tested using the standard dissolution test given above.

The procedure is repeated using the active substance in the absence of the hydrophobic material in order to provide a basis for comparison. The resulting dried active substance is then tested using the standard dissolution test.

If the graph of concentration versus time for the active substance combined with the hydrophobic material shows that that active substance in that combination has dissolved more slowly than the active substance alone, the hydrophobic material is regarded as being suitable for delaying the dissolution of the active substance.

The degree to which the hydrophobic material delays the dissolution of the active substance is a measure of the efficiency of the hydrophobic material. In particular, where it is desired to measure the delayed release performance of a particular formulation, that can be done by carrying out the standard dissolution test given above on a sample of the microparticles to be tested and upon a (control) sample of the active substance. For a true comparison the particle size distribution of the particles of the active substance must be the same or similar in the sample of formulation to be tested as in the (control) sample of active substance. The rate of dissolution of the active substance in the microparticles to be tested as a percentage of the rate of dissolution of the active substance alone can then be calculated by the following formula:

$$\% \text{ rate of dissolution} = \frac{TA}{TF} \times 100$$

Where TA=time taken for the concentration of the active substance to reach a maximum for the sample of active substance alone.
Where TF=time taken for the concentration of the active substance to reach a maximum for the sample of the formulation to be tested.
Thus, for example, if the concentration of the active substance in the dissolution test on the formulation reached a maximum at 40 minutes and the concentration of the active substance alone reached a maximum at 10 minutes, the % rate of dissolution for the formulation would be 10/40×100=25%, corresponding to a decrease in the rate of dissolution of 75%.

An alternative method is to measure the contact angle. Additive materials having contact angles greater than 90° are also regarded as hydrophobic additive materials.

The invention claimed is:

1. A method of preparing microparticles for use in a pharmaceutical composition for pulmonary administration, comprising particles of active substance having, on their surfaces, particles of a hydrophobic material suitable for delaying the dissolution of the active substance, the method comprising milling particles of the active substance, wherein particles of hydrophobic material are present during said milling, so as to ensure a sufficient break-up of agglomerates of both active and hydrophobic material, dispersal and even distribution of the hydrophobic material over the active material, so that the particles of hydrophobic material become fused to the surface of the particles of active material, said microparticles exhibiting delayed dissolution as compared to the particles of the active substance, wherein the milling is dry milling, and wherein the milling comprises:
   (a) passing a mixture of particles of active material and particles of hydrophobic material in a fluid, through a constriction under pressure;
   (b) compressing a mixture of particles of active material and particles of hydrophobic material in a gap of predetermined width; or
   (c) jet milling particles of active material with particles of hydrophobic material.

2. A method of pulmonary administration of an active substance comprising a step of administering microparticles prepared according to the method of claim 1 to a person in need thereof.

3. A method according to claim 1, wherein the hydrophobic material comprises a $C_{10}$ to $C_{22}$ carboxylic acid, which may be linear or branched, saturated or unsaturated, or an ester, amide or a salt thereof.

4. A method according to claim 3, wherein the hydrophobic material comprises magnesium stearate.

5. A method according to claim 1, wherein the hydrophobic material comprises a phospholipid.

6. A method according to claim 1, wherein the microparticles comprise not more than 90% of the hydrophobic material based on the total weight of the microparticles.

7. A method according to claim 1, wherein the microparticles have a mass median aerodynamic diameter of not more than 10 μm.

8. A method according to claim 1, wherein the microparticles are agglomerated.

9. A method as claimed in claim 1, wherein the microparticles have at least a partial coating of a film-forming material.

10. A method as claimed in claim 1, in which the particles of hydrophobic material are present as a coating on the surface of the particles of active substance.

11. A method as claimed in claim 10, in which the coating is a discontinuous coating.

12. A method of preparing microparticles for use in a pharmaceutical composition for pulmonary administration, comprising particles of active substance having, on their surfaces, particles of a hydrophobic material suitable for delaying the dissolution of the active substance, the method comprising milling particles of the active substance, wherein particles of hydrophobic material are present during said milling, so as to ensure a sufficient break-up of agglomerates of both active and hydrophobic material, dispersal and even distribution of the hydrophobic material over the active material, so that the particles of hydrophobic material become fused to the surface of the particles of active material, said microparticles exhibiting delayed dissolution as compared to the particles of the active substance, wherein the milling is dry milling, and wherein the milling comprises:
   (a) passing a mixture of particles of active material and particles of hydrophobic material in a fluid, through a constriction under pressure;
   (b) compressing a mixture of particles of active material and particles of hydrophobic material in a gap of predetermined width; or
   (c) jet milling particles of active material with particles of hydrophobic material,
wherein the microparticles do not comprise an effective amount of an antimuscarinic agent.

13. Microparticles for use in a pharmaceutical composition, as made by the method of claim 1 or claim 12.

14. Microparticles as claimed in claim 13, wherein the hydrophobic material forms at least a partial coating on the surface of the active material.

15. Microparticles as claimed in claim 14, wherein the coating is a discontinuous coating.

16. A method of delaying a dissolution rate of an active substance of a pharmaceutical composition for pulmonary administration;
   the method comprising milling particles of an active substance, wherein particles of hydrophobic material are present during said milling, so as to ensure a sufficient break-up of agglomerates of both active and hydrophobic material, dispersal and even distribution of the hydrophobic material over the active material, so that the particles of hydrophobic material become fused to the surface of the particles of active material and administering the pharmaceutical composition to the lung of the patient, wherein the milling is dry milling, and wherein the milling comprises:
(a) passing a mixture of particles of active material and particles of hydrophobic material in a fluid, through a constriction under pressure;
(b) compressing a mixture of particles of active material and particles of hydrophobic material in a gap of predetermined width; or
(c) jet milling particles of active material with particles of hydrophobic material.

17. The method as claimed in claim 16 in which the dissolution rate is reduced by at least 20%.

18. A method as claimed in claim 16, wherein, upon inhalation of the microparticles, the active substance exerts its pharmaceutical effect over a period greater than the period over which the active substance exerts its pharmaceutical effect when inhaled alone.

19. The method of claim 18, wherein the active substance exerts its effect for a period greater than 12 hours.

* * * * *